United States Patent [19]

Schindler

[11] Patent Number: 4,734,368

[45] Date of Patent: Mar. 29, 1988

[54] PROCESS FOR THE BIOCONVERSION OF FUMARATE TO L-MALATE

[75] Inventor: Fritz Schindler, Gelsenkirchen, Fed. Rep. of Germany

[73] Assignee: Huels Aktiengesellschaft, Marl, Fed. Rep. of Germany

[21] Appl. No.: 654,070

[22] Filed: Sep. 24, 1984

Related U.S. Application Data

[63] Continuation-in-part of Ser. No. 592,977, Mar. 23, 1984.

[51] Int. Cl.$^4$ .................. C12P 7/46; C12R 1/645; C12R 1/665; C12R 1/71
[52] U.S. Cl. .................................. 435/145; 435/911; 435/914; 435/920; 435/929; 435/932; 435/933
[58] Field of Search ............... 435/145, 171, 232, 911, 435/914, 920, 929, 933, 932

[56] References Cited

U.S. PATENT DOCUMENTS

| | | | |
|---|---|---|---|
| 2,972,566 | 2/1961 | Kitahara | 435/145 |
| 3,063,910 | 11/1962 | Abe et al. | 435/145 |
| 3,922,195 | 11/1975 | Chibata et al. | |
| 3,980,520 | 9/1976 | Degen et al. | 435/145 |

FOREIGN PATENT DOCUMENTS

| | | | |
|---|---|---|---|
| 171990 | 3/1976 | Czechoslovakia | 435/145 |
| 884029 | 12/1961 | United Kingdom | 435/145 |
| 1426137 | 2/1976 | United Kingdom | 435/145 |

OTHER PUBLICATIONS

Sahni, V. P., "Some Effects of Organic Acid Supplementation on Utilization of Ammonium Compounds by Three Pathogenic Fungi", *Mycopathologia et Mycologia applicata*, vol. 43, pp. 4–48 (1971).
Kobayashi, G. S., "Fungi", Chap. 43, pp. 969–970 *Microbiology* (2nd ed.), Davis, et al. (Harper & Row, publ.) 1973.
Maruyama, et al. "Localization of Enzymes in the Mycelium and Microconidia of *Fusarium oxysporum*", *J. Bact.* 84: 307–312 (1962).
Davis, et al. "Organelle Isolation and Partial Characterization from Giant Cells of *Aspergillus niger*", *FEMS Lett.*, 1 (1977), pp. 51–54.
Jong, et al. ATCC Catalogue of Fungi/Yeasts (16th ed., 1984), pp. 26, 158, 197, and 331.
Moat, A. G., *Microbial Physiology* (Wiley-Interscience publ.) 1979, p. 158.
S. Takao and K. Hotta, "Conversion of Fumaric Acid Fermentation to L-Malic Acid Fermentation by the Association of *Rhizopus arrhizus* and *Proteus vulgaris*", *J. Ferment. Tech.*, vol. 54, 1976, pp. 197–199.
S. Takao, M. Tanida, and H. Kuwabara, "L-Malic Acid Production from Non-sugar Carbon Sources by *Paecilomyces varioti, J. Ferment. Tech.*, vol. 55, No. 2, 1977, pp. 196–199.
T. Furukawa, T. Nakahara and K. Yamada, "Studies on the Utilization of Hydrocarbons by Microorganisms, Part XX, Conversion of Fumaric Acid to L-Malic Acid by the Association of Two Kinds of Yeast", *Agr. Biol. Chem.*, vol. 34, No. 12, 1970, pp. 1833–1838.

*Primary Examiner*—Elizabeth Weimar
*Attorney, Agent, or Firm*—Millen & White

[57] ABSTRACT

L-malic acid is produced in a concentration of 170 to 400 g per liter and high yield by biotechnical conversion of fumaric acid neutralized with ammonium hydroxide in nutrient-free solution or suspension. Pure L-malic acid can be obtained economically therefrom with high efficiency in a quality suitable for food and pharmaceutical use. The fermentation can be carried out in simple vessels under non-sterile conditions. The conversion rate of the fumarate and the attainable concentration of L-malate are promoted by the ammonium ions.

30 Claims, No Drawings

PROCESS FOR THE BIOCONVERSION OF FUMARATE TO L-MALATE

This application is a continuation-in-part of application Ser. No. 592,977, filed Mar. 23, 1984.

BACKGROUND OF THE INVENTION

The invention relates to a process for the production of the pure L-isomer of malic acid from neutralized fumaric acid in highly concentrated aqueous solution by biotechnical conversion, at least half of the neutralized fumarate being in the form of $NH_4$-fumarate.

L-Malic acid is utilized in the food and pharmaceutical industries as a buffer material, a complexing agent, an acidulant, and a moisturizer. L-Malic acid, as a natural substance, is more suitable for these areas of application than the chemically accessible DL-isomer mixture of malic acid, producible, for example, by addition of water to maleic anhydride. The D-isomer of malic acid does not occur in nature; for this reason, chemically synthesized DL-malic acid is not always acceptable for food and pharmaceutical use.

Several methods are known for the biotechnical production of L-malic acid. In some of these processes (e.g., DE-AS No. 23 63 285), special bacteria convert fumaric acid into L-malic acid by the addition of water. U.S. Pat. No. 3,922,195 teaches immobilizing the bacterial cells, as well as use of the yeast *Pichia farinosa*. According to DAS No. 2,363,285, the process is carried out with free bacterial cells or according to DE-AS No. 24 15 310 with the enzyme fumarase, isolated from bacterial cells.

Conversion of glucose to L-malic acid with a combination of a fungus and a bacterium has been described [J. Ferment Technol. 54 (4): 197–204 (1976)]. In this method, the fungus makes fumaric acid from glucose, and this fumaric acid is then converted into L-malic acid by the bacterium.

The enzyme fumarase, effecting conversion of fumaric acid to L-malic acid, can be isolated in special processes from biological material, preferably the cell mass of microorganisms, and then can be used, in free or immobilized form to obtain L-malic acid from fumaric acid (DAS No. 2,415,310; Czechoslovakian Pat. No. 171,990).

In several processes, a large amount of a calcium compound is added to the fermentation batch, whereby the resultant L-malic acid is precipitated during the course of the fermentation itself, as calcium malate (e.g., the process of DOS No. 1,417,033).

Processes for the biotechnical manufacture of L-malic acid using fungi are also known. In these processes, the L-malic acid is essentially obtained by biochemical degradation and/or biosynthesis from the carbon source, e.g., molasses, sugar, ethanol, acetic acid, fed to the particular fungus [J. Ferment Technol. 55 (2): 196–199 (1977)]. These processes do not start directly with fumaric acid.

In the process described in U.S. Pat. No. 3,063,910 and the equivalent GB Pat. No. 884,029, the fermentation batch contains 10–15% of a sugar, and can also contain 1–10% of an organic acid, e.g., pyruvic acid or fumaric acid. However, in this fungal method, the added organic acid does not serve as a substrate for the synthesis of L-malic acid, but rather as a reaction accelerator for the biochemical transformation of the sugar substrate into L-malic acid. This is obvious especially from claim 4 of GB Pat. No. 884,029.

Fermentative conversion of n-paraffin into L-malic acid is possible by the association of two types of yeasts, wherein one type of yeast converts paraffin into fumaric acid, and the second type of yeast converts the resultant fumaric acid into L-malic acid [Agr. Biol. Chem. 34: 1833–1838 (1970)].

The biotechnical production of L-aspartic acid from hydrocarbons with ammonium fumarate as the intermediate stage is described in U.S. Pat. No. 4,013,508, in which a bacterium associated with a fungus is used. The ammonium fumarate is converted practically totally into L-aspartic acid, in which finally thermodynamic bases for formation of L-aspartic acid and against formation of L-malic acid from ammonium fumarate are mentioned.

Other data on the biotechnical conversion of ammonium fumarate to L-aspartic acid can be found in DE-PS No. 23 45 271 and BE No. 818,480.

The known methods for the biotechnical manufacture of L-malic acid have, inter alia, the following properties:

Biotechnical processes using bacteria are more difficult to handle than those using fungi. For example, separation problems can arise due to the small size of the bacteria. Furthermore, bacteria tend to form by-products, some of which are toxic. A particularly disturbing factor militating against use of L-malic acid in the pharmaceuticals area is LPS toxin (lipopolysaccharide toxin) formed by bacteria, which has a pyrogenic effect, and from which L-malic acid can be separated only by expensive process steps, e.g., ultrafiltration. In the methods described by U.S. Pat. No. 3,922,195, succinic acid occurs in small amounts as by-product, and can be separated from malic acid only with difficulty.

When using the isolated enzyme fumarase, the primary fumarase source is microbial cell mass. Before production of L-malic acid can be started, microbial cell mass must be grown and worked up, at considerable expense, to yield fumarase.

Immobilization of living cells or of the enzyme fumarase isolated from cells is an additional process step.

When fermenting in the presence of calcium ions in high concentration, the resultant L-malic acid is precipitated as calcium malate during the course of the fermentation; this leads to problems in effecting adequate agitation and aeration of the fermentation batch.

The attainable concentration of L-malic acid is generally comparatively low and lies markedly below 100 g per liter of fermentation batch except for the reactions described in U.S. Pat. No. 3,922,195 (immobilized microorganisms) and in DOS No. 1,417,033 (high calcium concentration and bacteria as source of fumarase).

Fermentation takes longer than three days. The large capacity of the bioreactors necessitated by this low yield results in high costs for apparatus; all the more so since the reactors are of an expensive construction to enable the process to be conducted free of contamination.

Although the term "fermentation" in technical literature has a relatively large spectrum of meanings, the expression "fermentation" in the context of the present invention means the fungal bioconversion of fumarate to L-malate, catalyzed by the enzyme fumarase, by incubation of a fumarase-containing microbial biomass, under bioconversion conditions. The term "culturing" means incubating the biomass from the inoculum in a nutrient medium, under conditions conducive to proliferation of the cell mass and consumption of the nutrients.

The production of the pure L-isomer of malic acid from neutralized fumaric acid by microbial fermentation by means of freely moving microorganisms in aqueous phase and of a concentration of L-malic acid at the harvest time of 100 to 170 g per liter of fermentation liquid is described in DE-OS No. 33 10 849.8. This process is marked by great productivity. The yield amounts to more than 77% of the theoretical yield. No D-malic acid is produced. The L-malic acid is obtained in a solution, whose working up comes very close to a quality suitable for food or pharmaceutical use. In this process the main amount of fumaric acid is used in the form of its sodium and/or potassium salt. DE-OS No. 33 10 849.8 corresponds to U.S. patent application Ser. No. 592,977, filed Mar. 23, 1984, the entire disclosure of which is incorporated herein by reference.

Although this process considerably exceeds the state of the art, the object is to improve it still more.

OBJECTS OF THE INVENTION

One object of the present invention is to develop a process for bioconversion of fumaric acid to L-malic acid in high yield and purity.

Another object of the invention is to reduce the capital investment required for L-malic acid production, especially with regard to the construction of bioreactors.

A further object of the invention is to simplify the processing steps for converting fumaric acid to pure L-malic acid.

Upon further study of the specification and appended claims, further objects and advantages of this invention will become apparent to those skilled in the art.

SUMMARY OF THE INVENTION

This object is achieved according to the invention by a process for producing pure L-malic acid from fumarate, which comprises the steps of incubating fumarase or cell-mass of a microorganism containing fumarase, under bioconversion conditions, in an aqueous solution of neutralized fumarate, at an initial fumarate concentration of 170–400 g per liter of liquid, calculated as fumaric acid and relative to the total volume of the cell-free solution, at least half of the neutralized fumarate being in the form of $NH_4$-fumarate, said incubation being maintained until the yield of L-malate, calculated as L-malic acid, reaches at least 0.9 g of L-malic acid per gram of reactant fumaric acid; and recovering resultant L-malic acid.

DETAILED DISCUSSION

The L-malic acid produced thereby is in the fermentation liquid in the form of the corresponding salt. In a preferred embodiment, only $NH_4OH$ is used for neutralizing the fumaric acid. In another embodiment, $NH_4OH$ and sodium hydroxide (NaOH) are used in a molar ratio of 2 to 1 for neutralizing. The amount of neutralized fumaric acid introduced can be greater than the amount that corresponds to saturation concentration. In this case, the fumarate is first introduced partly in undissolved form. The fumaric acid can also be added by portions to the fermentation vessel during the ongoing fermentation; then large concentrations of L-malic acid can be achieved without undissolved fumarate occurring at times.

The biotechnical conversion can be performed by means of microorganisms, preferably with fungi or by means of enzymes. The microorganisms can be freely moving or fixed.

The fungi can come preferably from one of the genera of Aspergillus, Penicillium, Paecilomyces, Taphrina, Helminthosporium, Pythium, Fusarium, Hyphopichia, especially from the species Aspergillus wentii, Aspergillus awamori, Penicillium nalgiovensis, Fusarium oxysporium, Hyphopichia burtoni. Fumarase can be used as enzyme; the enzyme is obtained from microorganisms which are suitable for conversion of fumarate to L-malate.

For carrying out the process, an aqueous solution or suspension of neutralized fumaric acid is produced, to which is added the cell mass grown separately and separated from the culture liquid. The concentration of the cell mass—calculated as dry mass—amounts to from 0.5 to 50 g per liter of the fermentation liquid containing fumarate. The fumarate is fermented for 6 to 48 hours at 20° to 60° C. under non-sterile conditions. The cell mass and L-malic acid are separated from the fermentation liquor by known processes.

A cell mass, freshly grown and separated from the culture liquid, can be used several times for fermentation—up to three times, preferably twice—in a fumarate solution or suspension newly introduced in each case.

Because of the ability of certain microorganisms, also or even preferably to convert fumaric acid to L-malic acid in the presence of high concentrations of $NH_4$, there is the possibility of considerably increasing the fumaric acid concentration at the beginning of the fermentation and correspondingly the L-malic acid concentration at the harvest time in comparison with processes known so far, since $NH_4$ fumarate dissolves significantly better in water than sodium or potassium fumarate.

The possibility of using $NH_4$ fumarate as substrate for production of L-malic acid is surprising, because, contrary to expectations:

there are fungi that tolerate such a high $NH_4$ concentration, corresponding, e.g., to a 1.8 normal $NH_4$ fumarate solution, in the process according to the invention, $NH_4$ fumarate is not converted to L-aspartic acid either directly (addition of $NH_3$ to fumaric acid) or indirectly (amination of oxaloacetic acid which is formed in the metabolism from fumaric acid by L-malic acid), $NH_4$ ions accelerate the biotechnical conversion of fumarate to L-malate, certain fungi, which do not at all or comparatively slowly convert sodium and/or potassium fumarate to the corresponding L-malate, become good L-malate producers if fumaric acid is presented to them as $NH_4$ salt.

Suitable microorganisms for use in the process of the invention can be isolated according to the following screening procedure:

On agar-plates which contain besides a carbon source, e.g., sucrose, and other nutrients, more $NH_4$ fumarate than can be dissolved, and which are therefore turbid due to undissolved fumarate, suspensions of earth samples or of other microorganisms-containing samples are spread out. During incubation on these agar-plates, only those microorganisms can grow and form cell colonies which accept high $NH_4$ fumarate concentrations and which do not use fumaric acid to an appreciable extent as a nutrient. Those microorganisms which metabolize fumaric acid will be inactivated after a short period of growth by the increasing pH-value due to the remaining alkaline component of the fumarate.

As L-malate is far more soluble in water than fumarate, among those microorganisms which show a clear zone around their colonies, microorganisms with high fumarate/L-malate conversion capability at high initial $NH_4$ fumarate concentrations can be detected.

From microbial culture collections also microbial strains can be obtained which are suitable for use in the process of the invention.

Exemplary strains, available from public depositories, and shown to be useful in the present method, include but are not limited to:
  Aspergillus wentii CBS 121.32
  Aspergillus phoenicis DSM 62068
  Aspergillus awamori DSM 63272
  Penicillium nalgiovensis CBS 352.48
  Hyphopichia burtoni DSM 70663
The depository abbreviations mean:
  CBS: Central Bureau of Mold Cultures (Netherlands),
  DSM: German Collection of Microorganisms (Germany)
Other strains can readily be obtained using the foregoing screening protocol.

The process according to the invention can be performed both by batch and continuously. The cells can, e.g., be retained in the fermentation vessel while the fermentation liquid is removed continuously and worked up to L-malic acid or the cells are continuously removed with the fermentation liquid and are returned to the fermentation vessel after separation from the liquid.

The biotechnical conversion of $NH_4$ fumarate proceeds faster than the conversion, e.g, of sodium (Na) fumarate. Thus, with the equally long fermentation time, greater concentrations of L-malic acid can easily be obtained at the harvest time.

The rate of the biotechnical conversion of fumaric acid to L-malic acid with the use of $NH_4$ fumarate and Na fumarate was determined in shaking flasks under the following conditions:

125 g/l of fumaric acid, neutralized with $NH_4OH$ or NaOH; temperature 27° C.; pH 8.0; incubation time 24 hours; cell mass 1 g/l (calculated as dry mass); cell mass obtained from an initial culture with 10 g of sugar per liter and 5 g of Na fumarate per liter (for adaptation of the fungi).

The concentration of L-malic acid in g/l at harvest time amounts, for example,

| with use of fungal strains | starting with 125 g/l fumaric acid | |
|---|---|---|
| | $NH_4$ salt | as Na salt |
| Fusarium oxysporium | 116 | 0 |
| Aspergillus wentii | 107 | 74 |
| Aspergillus phoenicis | 112 | 23 |
| Aspergillus awamori | 119 | 66 |
| Aspergillus versicolor | 122 | 35 |
| Aspergillus chrysogenum | 115 | 23 |
| Aspergillus niger | 106 | 20 |
| Penicillium nalgiovensis | 105 | 44 |
| Hyphopichia burtoni | 104 | 27 |

The conversion rate of $NH_4$ fumarate to L-malate is thus generally greater and with some fungal strains very much greater than the conversion rate of Na fumarate to L-malate.

Not only is the conversion rate with $NH_4$ fumarate greater than with other fumarates but the maximum obtainable final concentration of L-malic acid at the harvest time is also greater. In the case of neutralizing with NaOH a maximum of about 170 g/l of fumaric acid can be brought into solution, whereas in the case of neutralization with $NH_4OH$ a maximum of 210 g/l goes into solution. Since the concentration of L-malic acid at harvest time corresponds approximately to the concentration of fumaric acid introduced, about 210 g/l of L-malic acid can be obtained by neutralizing with $NH_4OH$, in comparison with about 170 g/l by neutralizing with NaOH.

With mixed salts, the fumaric acid amount to be put in solution, and therefore the amount of L-malic acid at harvest time, can be increased further. If the fumaric acid is neutralized with $NH_4OH$ and NaOH in the molar ratio of 2 to 1, about 240 g of fumaric acid can be brought into solution, with which an L-malic concentration of about 240 g/l can be achieved at harvest time.

Because of the great conversion rate of fumarate with great $NH_4$ concentrations, the amount of fumarate introduced does not all have to have gone into solution before the beginning of the conversion. Thus it will be possible to get close to the saturation concentration of the L-malate.

If, for example, 300 g of fumaric acid per liter is introduced and the pH of the suspension with $NH_4OH$ is set at 8, a part of the undissolved $NH_4$ fumarate is present as feedstock. With progressing conversion of the dissolved fumarate to L-malate, the fumarate that first was undissolved goes into solution and becomes accessible for conversion to L-malate. At harvest time, an L-malate concentration of about 300 g/l (calculated at L-malic acid) is obtained.

The biotechnical production of L-malic acid from fumaric acid according to the invention is a two-stage process.

In stage 1 the cell mass is grown by known processes by consumption of nutrients under sterile conditions. The culture liquid contains a source of assimilable carbon and further no or only a small amount of neutralized fumaric acid. If fumaric acid is added, it serves for adapting of the microorganisms.

If during growth, no or almost no fumaric acid is present, the fungi preferably grow in pellet shape and are easy to separate. By growth of the fungi in culture liquid containing fumaric acid, the fungi grow preferably in form of threads and are hard to separate.

Because of the sterilizing of the culture liquid necessary in stage 1, the fumaric acid optionally added in this stage is preferably neutralized with NaOH or potassium (K) hydroxide. $NH_4$ fumarate can already have changed partially during heating. The fumaric acid can also be neutralized in stage 1 with $NH_4OH$ in the case of chemical sterilizing or sterilizing by filtering.

The fumarate is biotechnically converted to L-malate in stage 2 by the cell mass grown and separated from the culture liquid in stage 1. No sterile conditions are required for stage 2. At the beginning of the conversion, the fermentation liquid contains the fumarate in highly concentrated form.

Growth of the cell mass in stage 1 occurs as follows:
The nutrient solution contains the following nutrients per liter:
  30 g saccharose (as a source of assimilable carbon)

2 g diammonium hydrogen phosphate $(NH_4)_2HPO_4$
3 g ammonium sulfate $(NH_4)_2SO_4$
0.9 g magnesium sulfate $MgSO_4.7H_2O$
2 g potassium chloride KCl
30 mg iron(III) chloride $FeCl_3.6H_2O$ Up to 30 g/l—preferably up to 5 g/l—of fumarate can be added for adapting of the microorganisms. If the microorganisms need more active substance for growing (e.g., vitamins), the nutrient solution is also mixed with this active substance.

The nutrient solution is set at a pH of 2 to 9—preferably from 3 to 6—and sterilized. The carbon compounds required for growth of the fungus are sterilized either with the inorganic nutrients or, e.g., to avoid caramelizing phenomena in sugars, are sterilized separately. Besides saccharose, also corn meal, glucose, glycerin, n-paraffin, ethanol and other compounds containing carbon are suitable for fungal growth.

The sterilized nutrient solution, with inoculum of a fungus suitable for biotechnical conversion of fumaric acid to L-malic acid, is inoculated in an amount of 1 to 20% by volume, preferably 3 to 10%. The cell mass is grown under controlled conditions in regard to temperature, aeration and pH for 1 to 3 days with consumption of the added carbon compound. The growing temperature is 20° to 50° C., preferably 25° to 35° C. The pH is kept constant during growth by feeding of alkali base.

After completion of growth in stage 1, the culture liquid is separated into culture filtrate and cell mass by filtering or another known operation for liquid and solid separation.

The biotechnical conversion of fumarate to L-malate in stage 2 occurs, for example, as follows:

The cell mass from stage 1 (or a previous stage 2) is transferred to a solution or suspension of the fumarate. The amount of cell mass (calculated as dry substance) is 0.5 to 50 g/l of the feedstock. The fumarate is completely or predominantly introduced as $NH_4$ fumarate, optionally first partially in undissolved form. The fermentation liquid is gently stirred and aerated in a vessel, in which the fungal cells convert the fumarate to L-malate. The temperature is 20° to 60° C., preferably 30° to 45° C., the pH is 6 to 10, preferably 7 to 9. After 6 to 48 hours, the conversion ends even with great fumarate concentration. The amount of L-malic acid is approximately equal to the original amount of fumaric acid.

The vessel used in stage 2 can be very simply designed, since no devices for sterilizing or for achieving a high oxygen transfer rate are necessary. A vessel that is simple to clean and controllable by thermostat with stirring and aeration devices is sufficient. Gentle stirring is advisable to avoid sedimenting of the cell mass; gentle aeration is advisable to provide the cells with the oxygen necessary to maintain breathing.

The process according to invention has the following advantages:

$NH_4$ fumarate is converted faster than other fumarates, by which the space-time yield is improved.

The concentration of L-malic acid at harvest time is greater than in other known processes, which makes economical working up possible.

In the fermentation, highly concentrated L-malic acid precipitates in the form of its $NH_4$ salt in a liquid which, outside of this $NH_4$ malate, contains only residues of unconverted $NH_4$ fumarate and cell mass, which considerably facilitates working up.

The fumarate is converted with higher yield of L-malate; the amount of L-malic acid produced is approximately exactly as great as the amount of initial fumaric acid introduced, and at least 0.9 g per gram of fumaric acid.

The biotechnical conversion occurs in a simply designed vessel, which uses no devices for achieving and maintaining sterile conditions and for achieving a high oxygen transfer rate and thus is economical to produce and operate.

No D-malic acid is produced.

L-malic acid is obtained in a liquid, whose working up comes very close to a quality suitable for food and pharmaceutical use, e.g., in regard to the absence of LPS toxin and succinic acid.

The separated cell mass can be used repeatedly.

The fumaric acid is converted to L-malic acid exclusively under optimal fermentation conditions; the optimal growth conditions for the fungus need not be taken into consideration in this connection.

The invention is illustrated by the following examples without being limited to them.

Growth of the cell mass

EXAMPLE A

To grow the cell mass in stage 1, a nutrient solution is prepared which contains per liter of drinking water.

30 g saccharose
3 g $(NH_4)_2SO_4$
2 g $(NH_4)_2HPO_4$
0.9 g $MgSO_4.7H_2O$
2 g KCl
30 mg $FeCl_3.6H_2O$
10 g Na fumarate A bioreactor with 8 liters of working volume is charged with 7.2 liters of this nutrient, sterilized and inoculated with 0.8 liter of inoculum of the fungus *Aspergillus wentii*. The growing conditions are:

aeration with 0.5 liter of air per liter of working volume of the bioreactor and minute (0.5 vvm)
mixer speed 500 revolutions per minute (blade mixer in combination with a draft tube)
temperature 30° C.
pH 7.0 (is kept constant by feeding of NaOH solution by control with pH electrode).

After 48 hours, 11.2 g of cell mass (calculated as dry mass) is produced per liter of culture liquid which is filtered off and washed.

EXAMPLE B

Cell mass of the fungus *Aspergillus awamori* is grown analogously with example A with the following variants:
the nutrient solution contains no fumarate
the pH is set at 6.0 and kept constant.

EXAMPLE C

Cell mass of the fungus *Penicillium nalgiovensis* is grown analogously to example A.

EXAMPLE D

Cell mass of the fungus *Hyphopichia burtoni* is grown analogously to example A, in which the nutrient solution contains 30 g/l of Na fumarate instead of 10 g/l of Na fumarate.

EXAMPLE E

Cell mass of the fungus *Fusarium oxysporium* is grown analogously to example A.

EXAMPLE F

Cell mass of the fungus *Aspergillus wentii* is grown analogously to example B, i.e., without fumarate in the nutrient solution.

Biotechnical conversion of fumaric acid to L-malic acid

EXAMPLE 1

The cell mass obtained from the 8-liter culture liquid of example A is suspended in 16 liters of a 210 g/l solution containing fumaric acid (neutralized with NH$_4$OH; pH=8.0) and incubated in a vessel that is gently stirred and aerated at 32° C. under non-sterile conditions. After 24 hours of incubation 213 g of L-malic acid per liter of fermentation liquid is produced.

EXAMPLE 2

Cell mass grown according to example F is suspended in 16 liters of a 240 g/l solution containing fumaric acid (neutralized with NH$_4$OH and NaOH in the molar ratio of 2 to 1). After 24 hours of incubation, 235 g of L-malic acid per liter of fermentation liquid is produced.

EXAMPLE 3

Cell mass grown according to example A is suspended in 16 liters of a 320 g/l solution/suspension containing fumaric acid (neutralized with NH$_4$OH). After 36 hours of incubation, 328 g of L-malic acid per liter of fermentation liquid is produced.

EXAMPLE 4

Cell mass grown according to example A is suspended in 8 liters of a 240 g/l solution containing fumaric acid (neutralized with NH$_4$OH NaOH in the molar ratio of 2 to 1). After 12 hours of incubation, 237 g of L-malic acid per liter of fermentation liquid is produced.

EXAMPLE 5

The cell mass separated from the fermentation liquid of example 1 is again suspended in 16 liters of a 210 g/l solution containing fumaric acid (neutralized with NH$_4$OH; pH=8.0); this cell mass is thus used twice for biotechnical conversion of fumarate to L-malate. After 36 hours incubation, 198 g of L-malic acid per liter of fermentation liquid is produced.

EXAMPLE 6

Cell mass grown according to example B is suspended in a vessel with 300 liters working volume in a 210 g/l solution containing fumaric acid (neutralized with NH$_4$OH; pH=8.0). The concentration of cell mass in the fumaric acid solution amounts to 30 g/l (calculated as dry mass). After 24 hours incubation, 205 g of L-malic acid per liter of fermentation liquid is produced.

EXAMPLE 7

Cell mass grown according to example E is suspended in a vessel with 300 liters working volume in a 210 g/l solution containing fumaric acid (neutralized with NH$_4$OH; pH=8.0) The concentration of the cell mass in the fumaric acid solution amounts to 30 g/l (calculated as dry mass). After 36 hours incubation, 207 g of L-malic acid per liter of fermentation liquid is produced.

EXAMPLE 8

Cell mass grown according to example C is suspended in 16 liters of a 240 g/l solution containing fumaric acid (neutralized with NH$_4$OH and NaOH in the molar ratio of 2 to 1). The concentration of the cell mass in the fumaric acid solution amounts to 6 g/l (calculated as dry mass). After 24 hours of incubation, 234 g of L-malic acid per liter of fermentation liquid is produced.

EXAMPLE 9

Cell mass grown according to example D is suspended in 16 liters of a 210 g/l solution containing fumaric acid (neutralized with NH$_4$OH; pH=8.5). The concentration of the cell mass in the fumaric acid solution amounts to 7 g/l (calculated as dry mass). After 36 hours incubation, 212 g of L-malic acid per liter of fermentation liquid is produced.

EXAMPLE 10

An NH$_4$ fumarate suspension with 400 g/l (calculated as fumaric acid) is introduced in a vessel and set at pH 8.0. The fumarate is first introduced partly in undissolved form. 35 g/l of cell mass (calculated as dry mass)—grown according to example A—is suspended in this liquid. After 36 hours incubation at 32° C., 378 g of L-malic acid per liter of fermentation liquid is produced.

EXAMPLE 11

An NH$_4$ fumarate solution with 190 g/l (calculated as fumaric acid) is introduced in a vessel and set at pH 8.0. 29 g/l of cell mass (calculated as dry mass)—grown according to example A—is suspended in this liquid. After 6 hours incubation at 34° C., 171 g of L-malic acid per liter of fermentation liquid is produced.

In all the examples the cell mass and L-malate are separated by known processes at the end of the fermentation. The cell mass is optionally used for a further fermentation, the L-malate is worked up to L-malic acid by known processes.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing L-malate from fumarate comprising incubating under bioconversion conditions a proliferated cell mass derived from a microorganism containing fumarase effective to convert exogenous fumarate to L-malate in an aqueous solution of fumarate, said solution containing the cell mass in a concentration of from about 0.5 to 50 g/l (calculated as dry mass) and an initial fumarate concentration of about 170–400 g per liter of liquid, calculated as fumaric acid and relative to the total volume of the solution, at least half of the fumarate being in the form of ammonium-fumarate, said incubation being maintained until the yield of L-malate, calculated as L-malic acid, reaches at least 0.9 g per gram of initial fumarate, calculated as fumaric acid.

2. A process of claim 1, further comprising, prior to said incubating step, proliferating a microbial cell mass, derived from a microorganism containing fumarase effective to convert exogenous fumarate to L-malate, in an aqueous solution containing a source of assimilable carbon and nutrients for said microorganism, and separating the proliferated cell mass from the culture liquid.

3. A process of claim 2, wherein said nutrient solution contains 1–30 g/l of fumarate; whereby said microorganism is adapted to effect bioconversion of fumarate.

4. A process of claim 2, wherein said assimilable carbon source is corn meal, glucose, sucrose, glycerol or ethanol.

5. A process of claim 1, wherein said incubation is maintained for 0.5–2 days, at 20°–50° C. and pH 3–9.

6. A process of claim 1, which further comprises recovering the freely moving cell mass produced during said bioconversion of fumarate to L-malate and using at least a portion thereof as the inoculum in at least one subsequent incubation for bioconversion of fumarate to L-malate, the initial concentration of fumarate, calculated as fumaric acid, being 170–400 g per liter of the cell-free solution, said subsequent incubation being maintained until the yield of L-malate, calculated as L-malic acid, reaches at least 0.9 g of L-malate per gram of fumarate.

7. A process of claim 1, which is performed under non-sterile conditions.

8. A process of claim 1, wherein said fungus does not use fumarate or L-malate as a nutrient.

9. A process of claim 1, wherein said fungus belongs to the genus Aspergillus, Pencillium, Paecilomyces, Helminthosporium, Pythium, Taphrina, Fusarium or Hyphopichia.

10. A process of claim 9, wherein said fungus belongs to the species *Aspergillus wentii, Penicillium nalgiovensis, Aspergillus awamori, Fusarium oxysporium* or *Hyphopichia burtoni*.

11. A process of claim 10, wherein said species is the type strain *Aspergillus wentii* Wehmer, C. Wehmer.

12. A process of claim 1, wherein said L-malate produced is free of lipopolysaccharide toxins and succinic acid.

13. A process of claim 1, wherein all of said fumarate is obtained by combining a solution of fumaric acid with $NH_4OH$.

14. A process of claim 1, wherein said fumarate is obtained by neutralizing the pH value of a solution of fumaric acid with $NH_4OH$ and $NaOH$ in a molar ration $NH_4OH/NaOH$ of 2/1.

15. A process of claim 1, wherein the initial concentration of fumarate exceeds the saturation concentration of the solution, a portion thereof being undissolved.

16. A process of claim 1, wherein said fumarate consists essentially of a solution of fumarate that is nutrient-free.

17. A process of claim 1, comprising, prior to said incubating step, proliferating a microbial cell mass, derived from a microorganism containing fumarase effective to convert exogenous fumarate to L-malate, in an aqueous solution containing a source of assimilable carbon and nutrients for said microorganism, and at most a small amount of fumarate, and separating the proliferated cell mass from the culture liquid.

18. A process of claim 17, wherein said nutrients comprise per liter of solution:
2 g $(NH_4)_2HPO_4$
3 g $(NH_4)_2SO_4$
0.9 g $MgSO_4$ $(7H_2O)$
2 g $KCl$
30 mg $FeCl_3$ $(6H_2O)$.

19. A process of claim 1, wherein solid fumaric acid and a neutralizing solution comprising $NH_4OH$ are simultaneously added to the incubation solution at least one time during the incubation.

20. A process according to claim 19, wherein said neutralizing solution further comprises $NaOH$.

21. A process of claim 20, wherein solid fumaric acid and the neutralizing solution are added a plurality of times until dissolved fumarate is formed in the aqueous solution.

22. A process according to claim 21, wherein the initial fumarate concentration is 300–400 g/l of liquid, calculated as fumaric acid and relative to the total volume of the cell-free solution.

23. A process of claim 1, wherein the fumarate is a mixture of ammonium— and sodium-fumarates.

24. A process according to claim 1, wherein the microorganism is a filamentous fungus.

25. A process according to claim 1, wherein the initial fumarate concentration is 208–400 g/l of liquid, calculated as fumaric acid and relative to the total volume of the cell-free solution.

26. A process according to claim 1, wherein the initial fumarate concentration is 210–400 g/l of liquid, calculated as fumaric acid and relative to the total volume of the cell-free solution.

27. A process according to claim 1, wherein the initial fumarate concentration is 240–400 g/l of liquid, calculated as fumaric acid and relative to the total volume of the cell-free solution.

28. A process according to claim 1, wherein the cell mass is a free moving cell mass.

29. A process for producing pure L-malic acid, comprising incubating under bioconversion conditions a proliferated cell mass derived from a microorganism containing fumarase effective to convert exogenous fumarate to L-malate in an aqueous solution of fumarate, said solution containing the cell mass in a concentration of from about 0.5 to 50 g/l (calculated as dry mass) and an initial fumarate concentration of about 170–400 g per liter of liquid, calculated as fumaric acid and relative to the total volume of the solution, at least half of the fumarate being in the form of ammonium-fumarate, said incubation being maintained until the yield of L-malate, calculated as L-malic acid, reaches at least 0.9 g per gram of initial fumarate, calculated as fumaric acid, and converting the L-malate to L-malic acid and recovering said L-malic acid.

30. A process according to claim 29, further comprising, prior to said incubation, proliferating a microbial cell mass, derived from a microorganism containing fumarase effective to convert exogenous fumarate to L-malate, in an aqueous solution containing a source of assimilable carbon and nutrients for said microorganism, and separating the proliferated cell mass from the culture liquid, and converting the L-malate to L-malic acid and recovering said L-malic acid.

* * * * *